United States Patent
Guan et al.

(12)

(10) Patent No.: US 12,064,412 B2
(45) Date of Patent: Aug. 20, 2024

(54) METHOD FOR PREPARING SOLUTION FORMULATION FOR AEROSOL INHALATION OF NARINGENIN

(71) Applicant: SUN YAT-SEN UNIVERSITY, Guangdong (CN)

(72) Inventors: Mingyi Guan, Guangdong (CN); Weiwei Su, Guangdong (CN); Hongliang Yao, Guangdong (CN)

(73) Assignee: SUN YAT-SEN UNIVERSITY, Guangzhou (CN)

( * ) Notice: Subject to any disclaimer, the term of this patent is extended or adjusted under 35 U.S.C. 154(b) by 234 days.

(21) Appl. No.: 16/976,728

(22) PCT Filed: Aug. 28, 2019

(86) PCT No.: PCT/CN2019/102948
§ 371 (c)(1),
(2) Date: Aug. 28, 2020

(87) PCT Pub. No.: WO2020/252912
PCT Pub. Date: Dec. 24, 2020

(65) Prior Publication Data
US 2023/0110326 A1    Apr. 13, 2023

(30) Foreign Application Priority Data
Jun. 21, 2019   (CN) .......................... 201910541928.3

(51) Int. Cl.
| | | |
|---|---|---|
| A61K 31/352 | (2006.01) |
| A61K 9/00 | (2006.01) |
| A61K 9/08 | (2006.01) |
| A61K 47/02 | (2006.01) |
| A61K 47/12 | (2006.01) |
| A61K 47/18 | (2017.01) |
| A61K 47/40 | (2006.01) |

(52) U.S. Cl.
CPC .......... *A61K 31/352* (2013.01); *A61K 9/0078* (2013.01); *A61K 9/08* (2013.01); *A61K 47/02* (2013.01); *A61K 47/12* (2013.01); *A61K 47/186* (2013.01); *A61K 47/40* (2013.01)

(58) Field of Classification Search
None
See application file for complete search history.

(56) References Cited

FOREIGN PATENT DOCUMENTS

| | | |
|---|---|---|
| CN | 1555793 A | 12/2004 |
| CN | 105866259 A | 8/2016 |

OTHER PUBLICATIONS

Lin. Journal of Ocular Pharmacology and Therapeutics, 2015, 31 (1), 51-56 (Year: 2015).*
Takahashi. Journal of Clinical Microbiology, 1984, 20(4), 608-613 (Year: 1984).*
International Search Report of PCT/CN2019/102948.
Written Opinion of PCT/CN2019/102948.

* cited by examiner

*Primary Examiner* — Noble E Jarrell

(57) ABSTRACT

The present invention discloses a solution formulation for aerosol inhalation of naringenin and preparation method thereof. The formulation is prepared from 1 part by weight of naringenin, 15-30 parts by weight of hydroxypropyl β-cyclodextrin, a buffer-salt solution and an appropriate amount of an excipient. The preparation method includes: preparing a buffer-salt solution of a pH value of 7-8.5 by using the buffer salt, adding the naringenin into the buffer-salt solution, then adding the hydroxypropyl β-cyclodextrin, shaking in a constant-temperature air bath till complete dissolving and coating, adding an appropriate amount of the excipient, filtering, filling and sterilizing. The present invention, by firstly increasing the solubility of the free naringenin in the solvent by adjusting the pH value, and then coating the naringenin with the hydroxypropyl β-cyclodextrin, significantly increases the overall concentration of the naringenin in the solvent.

7 Claims, 3 Drawing Sheets

METHOD FOR PREPARING SOLUTION FORMULATION FOR AEROSOL INHALATION OF NARINGENIN

CROSS-REFERENCE TO RELATED APPLICATIONS

This application is a national stage application of PCT Application No. PCT/CN2019/102948. This application claims priority from PCT Application No. PCT/CN2019/102948, filed Aug. 28, 2019, CN Application No. CN2019105419283 filed Jun. 21, 2019, the contents of which are incorporated herein in the entirety by reference.

Some references, which may include patents, patent applications, and various publications, are cited and discussed in the description of the present disclosure. The citation and/or discussion of such references is provided merely to clarify the description of the present disclosure and is not an admission that any such reference is "prior art" to the present disclosure described herein. All references cited and discussed in this specification are incorporated herein by reference in their entireties and to the same extent as if each reference was individually incorporated by reference.

FIELD

The present invention relates to a novel method for preparing naringenin formulation.

BACKGROUND

Naringenin is a flavanone-type compound, mainly exists in the pericarp and flesh of rutaceous plants such as grapefruit, tangerine and orange, and is the main active ingredient of the Chinese herbal drugs Pummelo Peel, Rhizoma Drynariae, Fructus Aurantii Immaturus and Fructus Aurantii. Naringenin can be used for the treatment of acute and chronic cough diseases, and has very good functions in relieving cough, eliminating phlegm and diminishing inflammation. The mechanism of cough relieving of naringenin is peripheral cough relieving, and as compared with the drugs of central cough relieving used clinically currently, naringenin has the advantages of no central action and no addiction. Therefore, naringenin has a good prospect in the application to the treatment of acute and chronic respiratory diseases.

Naringenin is very insoluble in water, so to increase the solubility of naringenin is the problem that is required to be solved firstly in the preparing of naringenin preparations. The traditional coating approach is to mix the drug and hydroxypropyl β-cyclodextrin in an aqueous solvent, wherein the solubilization effect is limited by the solubility of the drug itself in the solvent. It is also reported that the drug is firstly dissolved into ethanol and then mixed with hydroxypropyl β-cyclodextrin to obtain the inclusion compound, but, because the residue of the organic solvent in the obtained inclusion-compound solution, the populations that can use the preparation are limited.

The pharmacokinetic study on naringenin indicated that, after the oral administration of naringenin by a rat, the bioavailability, as calculated by the free naringenin, is approximately 4%. Furthermore, most of the drug is concentrated at the gastrointestinal tract, and only a small fraction can reach the lung, which limits the utilization of the efficacy of naringenin. An advantage of aerosol inhalation preparations is that the drug directly reaches the target sites, and, by the huge surface area of the air saccules of the lung, the rich blood capillary and the very small travelling distance, is quickly absorbed into the blood circulation, which has a quick efficacy. As compared with oral administration, the administration dosage can be greatly reduced. Aerosol inhalation is an ideal administration route for the treatment of respiratory diseases. Currently, there has not been a solution formulation for aerosol inhalation of naringenin in the market home and abroad.

SUMMARY

An object of the present invention is to, aiming at the problems of naringenin of a low solubility, and, in the oral administration route, a low bioavailability and a low drug concentration at the target sites, provide a method for preparing a solution formulation for aerosol inhalation of naringenin to improve its solubility, and increase the drug concentrations at the target organs by means of the administration mode of pulmonary inhalation.

The present invention is implemented by using the technical solution as defined in the appended claims.

The obtained solution formulation for aerosol inhalation is directly inhaled into the respiratory system in the atomized form by using an ultrasonic atomizer or an air-compression-type atomizer.

As compared with the prior art, the present invention has the following advantageous effects:

The present invention, coating and solubilizing naringenin by using hydroxypropyl β-cyclodextrin, is different from traditional coating techniques. The present invention, by firstly increasing the concentration of the free naringenin in the solvent by regulating and controlling the pH value of the solvent, and then adding the hydroxypropyl β-cyclodextrin for coating, enables the overall concentration of the naringenin in the solution to greatly increase. After the solution formulation for aerosol inhalation of naringenin prepared by using the present invention has been placed at a high temperature of 60° C. and an illumination of 4500±5001× for 10 days, all of its characters, amount and relevant components maintain stable.

The solution formulation for aerosol inhalation of naringenin prepared by the method of the present invention, by using the atomizer, in the form of aerosol, is inhaled via mouth or nose and delivered to the respiratory tract or the lung, and the drug directly acts on the target sites, which has a quick efficacy. As compared with oral administration, the drug concentrations at the target sites are high and the efficacy is quick, which can satisfy the demands on the preparations for the treatment of respiratory diseases to a larger extent.

The solution formulation for aerosol inhalation of naringenin prepared by using the present invention fills the blank in the market home and abroad currently, has a simple and environmentally friendly preparation process, employs economical and safe excipients, and is suitable for industrial production.

DETAILED DESCRIPTION OF THE EMBODIMENTS

Figure 1:
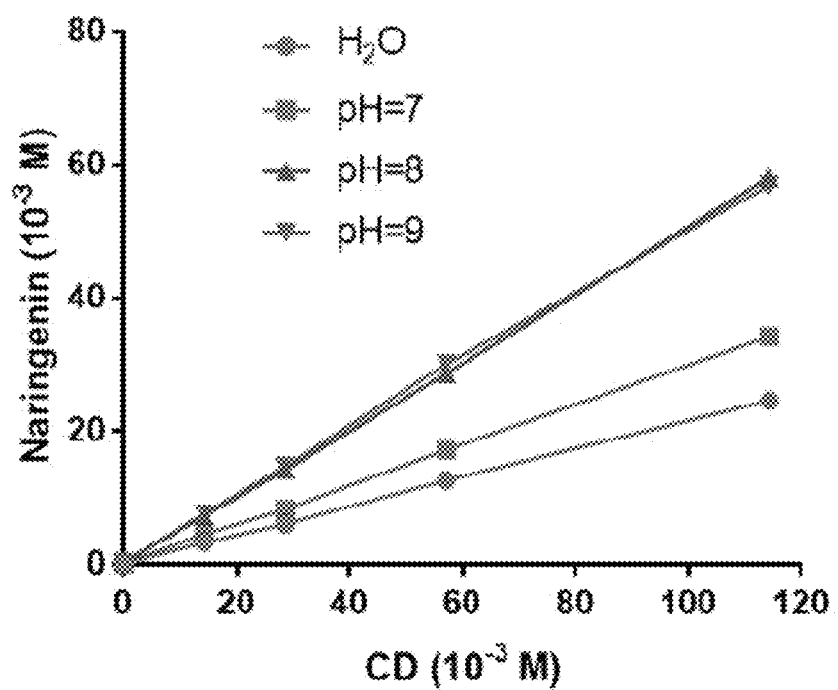
FIG. 1 is the curve diagram of the phase solubilities in environments of different pH values of the naringenin-hydroxypropyl-β-cyclodextrin inclusion compound.

The present invention will be further particularly described by using the following examples.

Example 1

Prescription:

| Component | Dosage |
|---|---|
| Naringenin | 100 mg |
| Hydroxypropyl β-cyclodextrin | 2 g |
| Potassium dihydrogen phosphate | 0.04 g |
| Dipotassium phosphate | 0.6 g |
| Sodium chloride | 0.6 g |
| Sodium sulfite | 0.05 g |
| Purified water | 100 mL |

Preparation method: dissolving the prescription amounts of the phosphates into the purified water, to prepare a buffer-salt solution of a pH value of 7.8-8.0, adding the prescription amount of the naringenin, then adding the prescription amount of the hydroxypropyl β-cyclodextrin into the naringenin suspension, shaking in a constant-temperature air bath at 30° C. till the solution is clear, adding the prescription amounts of the sodium chloride and the sodium sulfite, stirring to dissolve, fine-filtering the obtained solution, filling, sealing and sterilizing.

Example 2

Prescription:

| Component | Dosage |
|---|---|
| Naringenin | 100 mg |
| Hydroxypropyl β-cyclodextrin | 1-5 g |
| Potassium dihydrogen phosphate | 0.7 g |
| Sodium hydroxide | Appropriate amount |
| Sodium chloride | 0.3 g |
| Sodium propyl hydroxybenzoate | 0.01 g |
| Purified water | 100 mL |

Preparation method: dissolving the prescription amount of the phosphate into the purified water, adding the sodium hydroxide to adjust the pH value of the solution to 7.4-7.6, adding the prescription amount of the naringenin, then adding the prescription amount of the hydroxypropyl β-cyclodextrin into the naringenin suspension, shaking in a constant-temperature air bath at 30° C. till the solution is clear, adding the prescription amount of the sodium propyl hydroxybenzoate, stirring to dissolve, fine-filtering the obtained solution, filling, sealing and sterilizing.

Example 3

Prescription:

| Component | Dosage |
|---|---|
| Naringenin | 100 mg |
| Hydroxypropyl β-cyclodextrin | 3 g |
| Borax | 57.2 mg |
| Calcium chloride | 294 mg |
| Sodium pyrosulfite | 0.1 g |
| Purified water | 100 mL |

Preparation method: dissolving the prescription amounts of the borax and the calcium chloride into the purified water, to prepare a buffer-salt solution of a pH value of 7.8-8.0, adding the prescription amount of the naringenin, then adding the prescription amount of the hydroxypropyl β-cyclodextrin into the naringenin suspension, shaking in a constant-temperature air bath at 30° C. till the solution is clear, adding the prescription amount of the sodium sulfite, stirring to dissolve, fine-filtering the obtained solution, filling, sealing and sterilizing.

Example 4

Prescription:

| Component | Dosage |
|---|---|
| Naringenin | 100 mg |
| Hydroxypropyl β-cyclodextrin | 2.5 g |
| Anhydrous citric acid | 1-2 g |
| Disodium hydrogen phosphate | 2.8 g |
| Sodium chloride | 0.8 g |
| Benzalkonium bromide | 0.1 g |
| Water | 100 mL |

Preparation method: dissolving the prescription amounts of the anhydrous citric acid and the disodium hydrogen phosphate into the purified water, to prepare a buffer-salt solution of a pH value of 7.4-7.8, adding the prescription amount of the naringenin, then adding the prescription amount of the hydroxypropyl β-cyclodextrin into the naringenin suspension, shaking in a constant-temperature air bath at 30° C. till the solution is clear, adding the prescription amounts of the sodium chloride and the benzalkonium bromide, stirring to dissolve, fine-filtering the obtained solution, filling, sealing and sterilizing.

Example 5: Study on Coating and Solubilization of Naringenin by Hydroxypropyl β-Cyclodextrin in Environments of Different pH Values Instruments and Reagents Instruments: a low-temperature stackable shaking table (Thermo Scientific company, the United States); and an ultraviolet-visible spectrophotometer (Agilent company, the United States)

Reference substance: naringenin (item No.: N5893-IG; content ≥95%; Sigma company, the United States). Test substance: naringenin (Xi'an Yhherb Limited Company; lot number: 20170520); hydroxypropyl β-cyclodextrin (Shandong Binzhou Zhiyuan Biotechnology Limited Company; and lot number: 20170617-1)

The process of the experimentation on the coating and solubilization of naringenin by hydroxypropyl β-cyclodextrin comprises:

preparing buffer-salt solutions of pH values of 4, 8 and 9 according to the method on a pharmacopoeia, adding different masses of the hydroxypropyl β-cyclodextrin into the buffer-salt solutions of the pH values of 4, 8 and 9 and ultrapure water, to prepare solutions of hydroxypropyl β-cyclodextrin of mass fractions (w/v) of 0, 2, 4, 8 and 16%, adding individually excessive naringenin, shaking in a constant-temperature shaking table at 25±1° C. at 200 rpm for 48 hours, taking out, standing, filtering by using a 0.45 μm microporous filter membranes, removing the primary filtrate, properly diluting the subsequent filtrate, and performing ultraviolet assay.

The detection of the naringenin concentrations of the solutions of hydroxypropyl β-cyclodextrin The detection method comprises, by using ultraviolet-visible spectrophotometry, measuring at the wavelength of 288 nm.

The Preparing of the Solutions:

The preparing of a stock solution of the reference substance comprises: precisely weighing an appropriate amount of the naringenin reference substance that has been dried at 105° C. to constant weight, placing in a 10 mL volumetric flask, and dissolving by using methanol to volume, to obtain a stock solution of the reference substance of the concentration of 1 mg/mL.

The preparing of standard samples comprises: precisely measuring and placing appropriate amounts of the stock solutions of the reference substance into volumetric flasks, and diluting by adding buffer-salt solutions of the corresponding pH values to obtain standard samples of the concentrations of 3, 5, 8, 10 and 16 μg/mL.

Experimental results: The curve diagram of the phase solubilities of hydroxypropyl β-cyclodextrin with naringenin in environments of different pH values can be seen in FIG. 1. In the environments of different pH values, hydroxypropyl β-cyclodextrin has an obvious effect of solubilization on naringenin in the whole concentration range of 0-16%, which expresses a linear relation, and belongs to AL-type phase-solubility curves. That indicates that in the concentration range the stoichiometric proportion of the joining of naringenin and hydroxypropyl β-cyclodextrin is 1:1. When the pH values are basic, the total naringenin concentrations in the solutions of hydroxypropyl β-cyclodextrin of the same concentration are approximately 3 times the total naringenin concentration in the environment of ultrapure water. The total naringenin concentrations in the environments of the pH values of 8 and 9 are close, which is speculated to be caused by, after the pH values have been adjusted, the ionization of the free naringenin, the increasing of the hydrophilicity and the decreasing of the coating efficiency of hydroxypropyl β-cyclodextrin. By comprehensively considering the effect on solubilization by naringenin and the irritative effect on lung by too basic pH values, the optimum pH value is selected as in the range of 7-8.5.

Example 6: Study on the In Vivo Pharmacokinetics of Rats of the Solution Formulation for Aerosol Inhalation of Naringenin Instruments and Reagents Instruments: 1200SL HPLC-6410 QQQ liquid chromatography-mass spectrometry (Agilent company, the United States); centrifuge 5415 R desktop high-speed refrigerated centrifuge (Eppendorf company, Germany); VortexGenie 2 Vortexer (Scientific Industries company, the United States); Simplicity ultrapure water producer (Millipore company, the United States); HWS24 model electrically heated thermostatic water bath (Shanghai Yiheng Instruments Co., Ltd.); KQ-250DE model digitally controlled ultrasound cleaner (Kunshan Ultrasonic Instruments Co., Ltd.); BP211D electronic analytical balance (Sartorius company, Germany); EYELA MG-2200 model termovap sample concentrator (EYELA); and pipette (Eppendorf company, Germany)

Reference substance: naringenin (item No.: N5893-IG; content ≥95%; Sigma company, the United States); and isoquercitrin (item No.: 17793-50 mg; content ≥90%). Test substance: naringenin (Xi'an Yhherb Limited Company; lot number: 20170520); and hydroxypropyl β-cyclodextrin (Shandong Binzhou Zhiyuan Biotechnology Limited Company; lot number: 20170617-1)

Methanol (LC/MS grade; Fisher Scientific company), ethyl acetate (chromatographic grade; B&J company), methanoic acid (MS grade; Fluka company), β-glucuronidase (Type H-1; SigmaAldrich company), and ultrapure water used as the water.

Animal: SD rats (SPF grade), provided by Guangdong Medical Laboratory Animal Center.

The design of the administration method and the collection of the blood sample and the lung tissue for the pharmacokinetic experimentation Single administration is employed by using 60 SD rats, each of which has a body weight of 200±20 g. The rats are divided randomly into 10 groups, which are intratracheal-instillation administration groups of 8 time points, one caudal-vein administration group and one blank group. The rats, within one day before the experiment, are not supplied with food for 12 h and can freely drink water. The administration dosage is 0.4 mg/kg. At the predetermined time points (5, 10, 15, 30, 60, 120, 240 and 480 min), blood is taken at the aortas or the orbit, placed into a centrifuge tube treated by heparin sodium, and centrifuged at 3000 rpm for 10 min, and the supernatant plasma is taken and stored in a refrigerator at −80° C. The rats of the intratracheal-instillation group are taken blood at the corresponding time points and then put to death by using cervical dislocation, the lung tissues are taken out, washed by using normal saline, dried by using a filter paper, and stored in a refrigerator at −80° C.

The measurement of the blood concentration of naringenin

Detection Conditions

The chromatographic conditions: a Welch NarrowBore HPLC Guard Column (2.1×10 mm, 3 μm) is employed as the pre-column, an Agilent Poroshell 120 EC-C18 (3.0×30 mm, 2.7 μm) is used as the chromatographic column, the mobile phase is methanol-water (40:60; both containing methanoic acid of @=0.1%), the flow rate is 0.4 mL/min, and the column temperature is 40° C. The mass spectrometry conditions: Capillary-4000V, Drying Gas-10 L/min, Neb Pressure-25 Psi, Gas Temp-350° C. The detection was performed by using electrospray anion (ESI−) and multiple-reaction monitoring (MRM) mode. Nitrogen is used as the spray gas and the auxiliary gas for quantitative analysis and qualitative detection of ion pair. The quantitative ion pairs and the corresponding parameters are as follows: naringenin m/z 270.9/150.7, Fragmentor 100V, Collision Energy 12V; and isoquercitrin (internal standard) m/z 463.1/299.8, Fragmentor 128V, Collision Energy 24V.

The Preparing of the Solutions

The preparing of a stock solution of the reference substance comprises: precisely weighing an appropriate amount of the naringenin reference substance that has been dried at 105° C. to constant weight, placing in a 10 mL volumetric flask, and dissolving by using methanol to volume, to obtain a stock solution of the calibration standard sample of the concentration of 1 mg/mL. Moreover, a stock solution of the quality-control sample is prepared by using the same approach, and is stored at 4° C. for reservation.

The preparing of the internal-standard solution comprises: precisely weighing an appropriate amount of the isoquercitrin reference substance that has been dried at 105° C. to constant weight, placing in a 10 mL volumetric flask, and dissolving by using methanol to volume, to obtain a stock solution of the internal standard of the concentration of 1 mg/mL. Moreover, a stock solution of the quality-control sample is prepared by using the same approach, and is stored at 4° C. for reservation. Before the sample treatment, the stock solution is diluted by using 60% methanol-water to 1 µg/mL, to be used as the internal-standard working solution.

The preparing of the β-glucuronidase solution comprises: precisely weighing an appropriate amount of β-glucuronidase, and dissolving by using a 0.2 mol/L acetic-acid buffer solution (pH=5.0), to obtain a β-glucuronidase solution of the concentration of 10 Unit/µL.

The Preparing of the Samples

The preparing of the calibration standard sample comprises: taking an appropriate amount of the stock solution of the calibration standard sample of naringenin, diluting by using 60% methanol-water to obtain working solutions of the calibration standard sample of the naringenin concentrations of 40, 100, 200, 1000, 2000, 4000, 10000 and 20000 ng/mL, taken 100 µL of a blank plasma, then adding individually 5 µL of the working solutions of the calibration standard sample of the corresponding concentrations, and vortex-stirring for 5 min, to obtain calibration standard samples of plasma of the concentrations of the target analyte naringenin of 2, 5, 10, 50, 100, 200, 500 and 1000 ng/mL. A blank sample (a treated substrate sample not containing the analyte and the internal standard) and a zero-concentration sample (a treated substrate containing the internal standard) are prepared at the same time.

The preparing of the quality-control samples (QC) comprises: taking an appropriate amount of the stock solution of the quality-control sample of naringenin, diluting by using 60% methanol-water to obtain working solutions of the quality-control sample of the naringenin concentrations of 320, 1600 and 16000 ng/mL, taking 100 µL of a blank plasma, then adding individually 5 µL of the working solutions of the quality-control sample of the corresponding concentrations, and vortex-stirring for 5 min, to obtain quality-control samples of plasma of the concentrations of the target analyte naringenin of 500, 1000 and 2000 ng/mL.

The preparing of the plasma sample comprises: taking 100 µL of the plasma sample, adding 5 µL of methanol-water of Ø=60%, then adding 10 µL of the β-glucuronidase solution (10 Unit·µL$^{-1}$), stirring uniformly, placing in a water bath at 37° C. for 2 h, taking out, adding 5 µL of the internal-standard working solution, stirring uniformly, adding 1000 µL of ethyl acetate, vortex-stirring for 1min, centrifuging at 10000 r·min$^{-1}$ for 10 min (4° C.), removing the supernatant, blowing by using nitrogen to dry, then redissolving by adding 100 µL of the mobile phase, sonicating for 5 min, vortex-stirring for 5 min, centrifuging at 13000 r·min$^{-1}$ for 45 min (20° C.), taking 10 µL of the supernatant, and injecting the sample.

Figure 2:
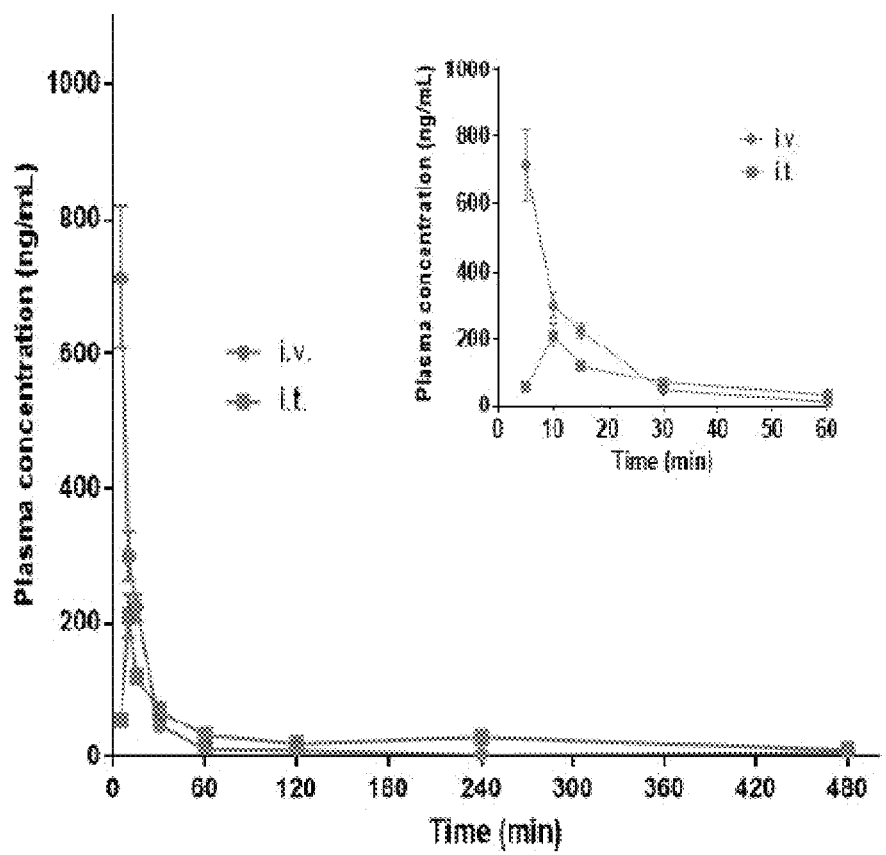
FIG. 2 is the drug-time curve diagrams of the intratracheal instillation administration and the vein administration of the solution formulation for aerosol inhalation of naringenin on SD rats (n=6)

The pharmacokinetic parameters are from the statistic result of a DAS2.0 software Experimental Results The pharmacokinetic parameters and the drug-time curve diagrams after the intratracheal-instillation administration and the caudal-vein injection administration of the solution formulation for aerosol inhalation of naringenin can be seen in Table 1 and FIG. 2. After the intratracheal-instillation administration, the naringenin is quickly absorbed into the blood circulation, which reaches $T_{max}$ at 10 min, which is close to the $T_{max}$ (5 min) of the caudal-vein injection administration, which demonstrates the characteristic of quick absorption of lung administration. The bioavailability of the intratracheal-instillation administration is approximately 87%, which is greatly improved as compared with that of oral administration.

TABLE 1

Comparison of the pharmacokinetic parameters after the intratracheal-instillation administration and the caudal-vein injection administration of the solution formulation for aerosol inhalation of naringenin (mean ± SD, n = 6)

| Pharmacokinetic parameter | Administration route | |
| --- | --- | --- |
| | Intratracheal instillation | Caudal-vein injection |
| $C_{max}$ (ng/mL) | 217.856 ± 66.352 | 713.119 ± 258.564 |
| $T_{max}$ (min) | 10 | 5 |
| $t_{1/2}$ (min) | 249.039 ± 127.842 | 134.735 ± 53.94 |
| AUC0-t (µg/L*min) | 14014.34 ± 2248.23 | 16154.53 ± 5174.882 |
| Bioavailability (%) | 86.75 | |

Figure 3:
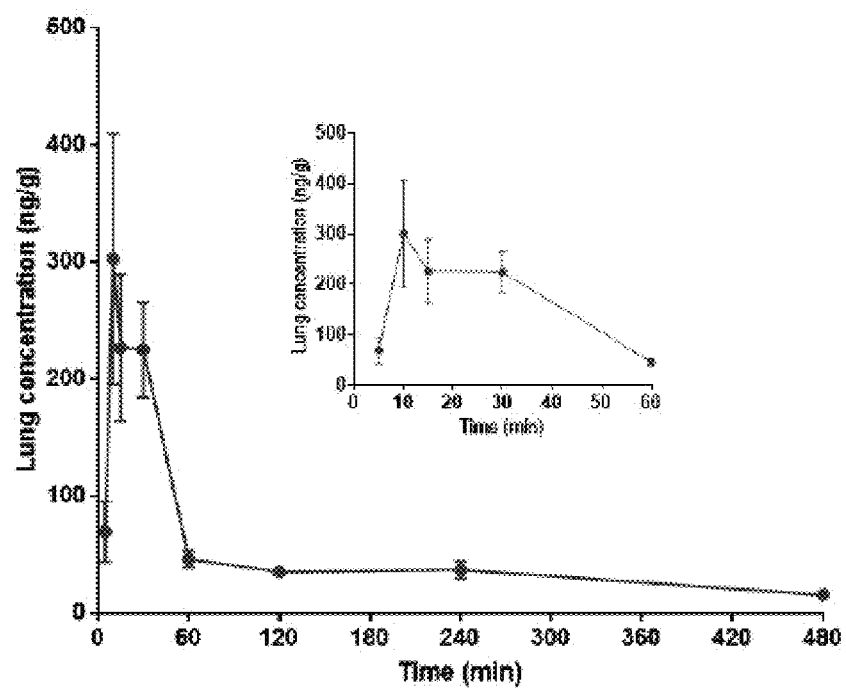
FIG. 3 is the curve diagram of the drug concentration of the lung tissue homogenate of the SD rats after the intratracheal instillation administration.

The pharmacokinetic parameters and the drug-time curve diagrams of the lung tissue after the intratracheal-instillation administration of the solution formulation for aerosol inhalation of naringenin can be seen in Table 2 and FIG. 3. After the intratracheal-instillation administration, the concentration of the naringenin in the lung reaches $T_{max}$ at 10 min. As compared with the pharmacokinetic parameters after the naringenin of an oral dosage of 21 mg/kg as reported by documents (AUC0-t (ng/g*min)=15080.4, $C_{max}$ (ng/g)=54.76, and $T_{max}$ (min)=120 min), intratracheal-instillation administration, while its administration dosage is far less than the oral dosage (which is, as converted, approximately 1/50 of that of oral administration), has a higher absorption of the drug at the target organs, and the $C_{max}$ (ng/g) has been significantly improved.

TABLE 2

The pharmacokinetic parameters of the lung tissue after the intratracheal-instillation administration of the solution formulation for aerosol inhalation of naringenin:

| Pharmacokinetic parameter | Intratracheal instillation |
| --- | --- |
| $C_{max}$ (ng/g) | 302.0945 |
| $T_{max}$ (min) | 10 |
| $t_{1/2}$ (min) | 279.174 |
| AUC0-t (ng/g*min) | 22691 |

What is claimed is:

1. A method for preparing a solution formulation for aerosol inhalation of naringenin, wherein the formulation is prepared from the following components: 1 part by weight of naringenin, 15-30 parts by weight of hydroxypropyl β-cyclodextrin and a buffer salt and an excipient, wherein the method comprises the steps of: preparing a buffer-salt solution of a pH value of 7-8.5 by using the buffer salt, adding the naringenin into the buffer-salt solution, then adding the hydroxypropyl β-cyclodextrin, shaking in a constant-temperature air bath till complete dissolving and coating, adding the excipient, and dissolving the excipient.

2. The method for preparing the solution formulation for aerosol inhalation of naringenin according to claim 1, wherein the buffer salt comprises one or more of phosphate, borate, citrate, hydrochloride, carbonate and acetate.

3. The method for preparing the solution formulation for aerosol inhalation of naringenin according to claim 1, wherein the excipient comprises one or more of an isosmotic adjusting agent, an antioxidant and a preservative.

4. The method for preparing the solution formulation for aerosol inhalation of naringenin according to claim 3, wherein the isosmotic adjusting agent comprises an inorganic-salt-type isosmotic adjusting agent or a saccharide-type isosmotic adjusting agent.

5. The method for preparing the solution formulation for aerosol inhalation of naringenin according to claim 4, wherein the inorganic-salt-type isosmotic adjusting agent is one or more of sodium chloride, magnesium chloride and calcium chloride, and an amount of the inorganic-salt-type isosmotic adjusting agent contained by each unit of the formulation is 0.2-0.9% by mass; and the saccharide-type isosmotic adjusting agent is one or more of glucose, fructose and mannose, and an amount of the saccharide-type isosmotic adjusting agent contained by each unit of the formulation is 2-10% by mass.

6. The method for preparing the solution formulation for aerosol inhalation of naringenin according to claim 3, wherein the antioxidant comprises one or more of vitamin c, sulfurous acid, sulfite, bisulfite, pyrosulfite, sodium thiosulfate, gallate esters, tartaric acid, and ascorbic acid and salts thereof; and an amount of the antioxidant contained by each unit of the formulation is 0.01-0.1% by mass.

7. The method for preparing the solution formulation for aerosol inhalation of naringenin according to claim 3, wherein the preservative comprises one or more of p-hydroxybenzoate esters, benzoic acid and salts thereof, benzoate esters, sorbic acid and salts thereof, and benzalkonium bromide, and an amount of the preservative contained by each unit of the formulation is 0.01-0.1% by mass.

\* \* \* \* \*